(12) United States Patent
Bala

(10) Patent No.: US 12,036,333 B2
(45) Date of Patent: Jul. 16, 2024

(54) STERILIZATION PROCESS CHALLENGE DEVICE

(71) Applicant: American Sterilizer Company, Mentor, OH (US)

(72) Inventor: Harry Bala, South Barrington, IL (US)

(73) Assignee: American Sterilizer Company, Mentor, OH (US)

( * ) Notice: Subject to any disclaimer, the term of this patent is extended or adjusted under 35 U.S.C. 154(b) by 402 days.

(21) Appl. No.: 17/375,086

(22) Filed: Jul. 14, 2021

(65) Prior Publication Data
US 2022/0111100 A1    Apr. 14, 2022

Related U.S. Application Data

(60) Provisional application No. 63/149,784, filed on Feb. 16, 2021, provisional application No. 63/055,553, filed on Jul. 23, 2020.

(51) Int. Cl.
*A61B 50/30* (2016.01)
*A61L 2/28* (2006.01)

(52) U.S. Cl.
CPC ................ *A61L 2/28* (2013.01); *A61B 50/30* (2016.02)

(58) Field of Classification Search
CPC .................................... A61L 2/28; A61B 50/30
See application file for complete search history.

(56) References Cited

U.S. PATENT DOCUMENTS

| | | |
|---|---|---|
| 4,154,342 A | 5/1979 | Wallace |
| 4,853,013 A | 8/1989 | Rio |
| 4,914,034 A * | 4/1990 | Welsh ...................... C12Q 1/22 435/31 |
| 5,167,923 A | 12/1992 | Van Iperen |
| 5,801,010 A | 9/1998 | Falkowski et al. |
| 5,866,356 A | 2/1999 | Albert et al. |
| 5,955,296 A | 9/1999 | Roll |
| 6,391,541 B1 | 5/2002 | Petersen |
| 7,247,482 B2 | 7/2007 | Lemus et al. |
| 7,718,125 B2 | 5/2010 | Bala |
| 7,790,105 B2 | 9/2010 | Bala |
| 7,875,239 B2 | 1/2011 | Bancroft |

(Continued)

FOREIGN PATENT DOCUMENTS

| | | |
|---|---|---|
| EP | 0433053 A1 | 6/1991 |
| EP | 1201255 A2 | 5/2002 |

OTHER PUBLICATIONS

International Preliminary Report on Patentability issued by WIPO on Feb. 2, 2023 in connection with PCT/US2021/041591.

(Continued)

*Primary Examiner* — Jill A Warden
*Assistant Examiner* — Michael Stanley Gzybowski
(74) *Attorney, Agent, or Firm* — Levenfeld Pearlstein, LLC

(57) ABSTRACT

A sterilization challenge device for verifying the efficacy of a sterilization process includes a container, an insert member, a sterilization indicator, and a cap. The container includes an open end, a closed end, a chamber configured to contain the biological indicator and the insert member, and at least one hole arranged proximate the open end. The cap is configured to engage with the container to close the open end, and the at least one hole is configured to provide a flow path for the gaseous sterilant into the chamber.

17 Claims, 9 Drawing Sheets

(56) References Cited

U.S. PATENT DOCUMENTS

| | | |
|---|---|---|
| 8,486,691 B2 | 7/2013 | Larson et al. |
| 9,017,994 B2 | 4/2015 | Franciskovich et al. |
| 2013/0230910 A1 | 9/2013 | Christensen et al. |
| 2015/0231628 A1 | 8/2015 | Nozaki |
| 2015/0335777 A1 | 11/2015 | Robbins et al. |
| 2016/0103043 A1 | 4/2016 | Skarping |
| 2017/0304476 A1 | 10/2017 | Taggart |
| 2018/0353889 A1* | 12/2018 | Turbett ............ B01D 46/62 |
| 2019/0106725 A1 | 4/2019 | Cregger et al. |
| 2019/0307910 A1 | 10/2019 | Bala |
| 2020/0165658 A1 | 5/2020 | Bala et al. |

OTHER PUBLICATIONS

International Search Report issued by ISA/EPO in connection with PCT/US2021/041591 on Nov. 3, 2021.

Written Opinion issued by ISA/EPO in connection with PCT/US2021/041591 on Nov. 3, 2021.

* cited by examiner

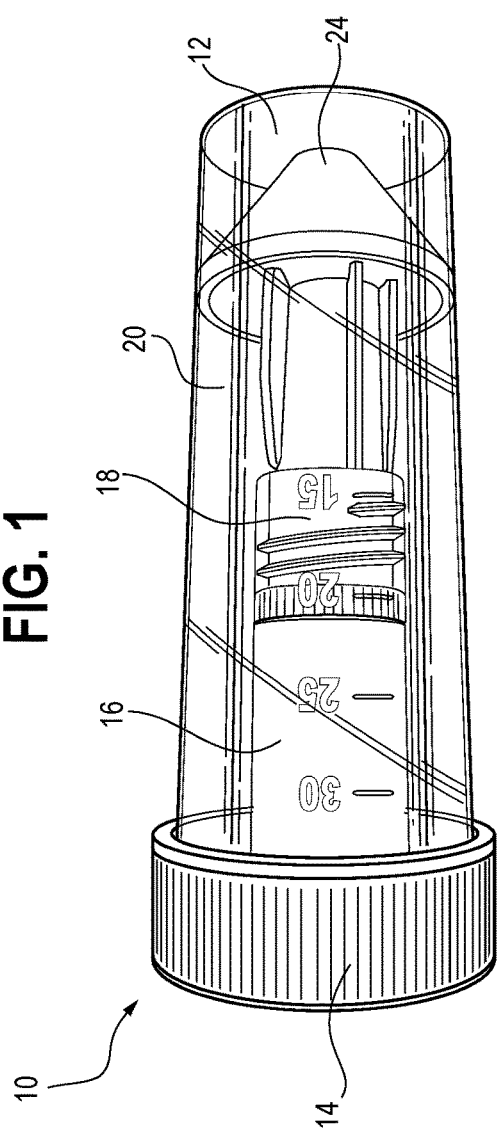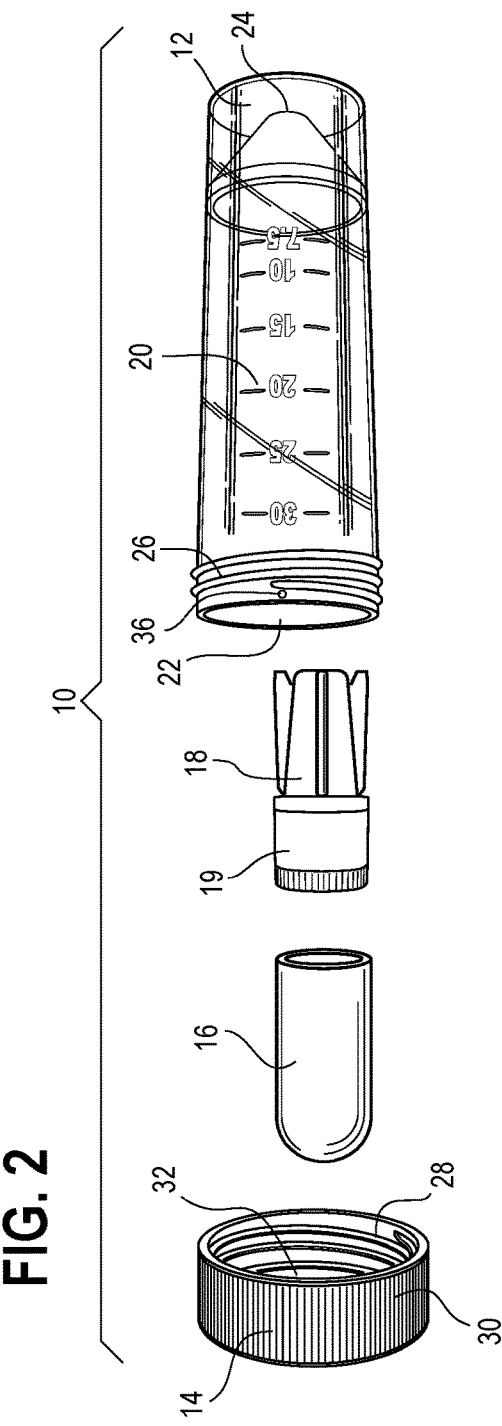

STERILIZATION PROCESS CHALLENGE DEVICE

CROSS-REFERENCE TO RELATED APPLICATION DATA

This application claims the benefit of and priority to Provisional U.S. Patent Application Ser. No. 63/055,553, filed Jul. 23, 2020, titled Sterilization Process Challenge Device, and Provisional U.S. Patent Application Ser. No. 63/149,784, filed Feb. 16, 2021, titled Sterilization Process Challenge Device, the disclosures of which are incorporated herein in their entireties.

BACKGROUND

The present invention is directed to a sterilization process challenge device for verifying the efficacy of a sterilization process.

U.S. Pat. No. 9,017,994, which is assigned to the Applicant of the present application and incorporated herein by reference, discloses a sterilization test pack including a biological indicator and a chemical indicator. The sterilization test pack also includes at least one external channel providing a restricted flow path(s) to the biological and chemical indicators, in which the at least one channel is defined by a groove(s) or indentation(s) having a depth, a width, and a length. U.S. Pat. No. 7,790,105, which is also assigned to the Applicant of the present application and incorporated herein by reference, discloses a sterilization challenge specimen holder including a holder configured to hold a sterilization indicator, such as a biological indicator, and a plug including grooves configured to provide a restricted flow path(s) to the sterilization indicator. Further, US Patent Application Publication No. 2019/0307910, which is assigned to the Applicant of the present application and incorporated herein by reference, discloses a sterilization challenge device that includes a filter assembly comprising at least one filter member and at least one gasket, which is configured to restrict flow of steam or gaseous sterilant into a chamber containing a sterilization indicator.

Accurate and cost effective verification of sterilization processes is important for obvious reasons. The present disclosure provides an improved sterilization process challenge device for verifying the efficacy of gas sterilization processes.

BRIEF SUMMARY

In one aspect, a sterilization challenge device for verifying the efficacy of a sterilization process may comprise a container, an insert member, a sterilization indicator, and a cap. The container may include a wall, an open end, a closed end, a chamber configured to contain the sterilization indicator and the insert member, and at least one opening defined through a thickness of the wall proximate the open end. The cap may be configured to engage with the container to close the open end. The at least one opening may be configured to provide a flow path for gaseous sterilant into the chamber when the container is closed with the cap. The insert member may include a closed end, an open end, and a hollow space defined therein. In an embodiment, the at least one opening may include a single hole having a diameter of about 0.014 inches or a single hole having a diameter of about 0.016 inches Alternatively, the sterilization challenge device may include a spacer member instead of the at least one opening defined through the wall of the container. The spacer member may be attached to the container to cover a portion of an open-end periphery of the container and configured to create a flow path for a gaseous sterilant to flow into the chamber when the open end of the container is closed with the cap. Such a sterilization challenge device may or may not include the insert member. In an embodiment, the spacer member may be formed from a tape having a thickness of about 8 mil to about 10 mil. In another embodiment, the spacer member may be formed from a tape having a thickness of about 5 mil.

In some embodiments, the sterilization indicator may be a biological indicator. In such embodiments, the insert member and the biological indicator may be arranged in the chamber, such that the insert member generally sits on top of the biological indicator, wherein the insert member is arranged adjacent the open of the container and the biological indicator is arranged adjacent the closed end of the container. Alternatively, the biological indicator may be placed on top of the insert member, wherein the biological indicator is arranged adjacent the open end of the container and the insert member is arranged adjacent the closed end of the container.

In an embodiment, the insert member and the biological indicator may be provided as a biological indicator assembly, wherein a portion of the biological indicator is received in the insert member and covered by the insert member. For example, a body portion of the biological indicator containing microorganism may be received in the insert member. In such an embodiment, the insert member may include at least one hole configured to provide a flow path for gaseous sterilant into the biological indicator assembly In an embodiment, the at least one hole of the insert member may include a single hole having a diameter of about 1/16 inches. In some embodiments, the insert member and the biological indicator may be held together with an indicator tape. The insert member may be formed from polyvinyl chloride and may have a generally cylindrical shaped body.

In any of the foregoing embodiments, the container may be formed from polypropylene and may have a generally cylindrical shaped body. In an embodiment, the container may include at least one external thread arranged proximate the open end of the container, and the cap may include at least one internal thread arranged along an outer wall and configured to engage the at least one external thread. For example, the container may include double external threads, and the cap may include double internal threads configured to engage with the double external threads. The gaseous sterilant may be hydrogen peroxide or ethylene oxide.

Other aspects, objectives and advantages will become more apparent from the following detailed description.

BRIEF DESCRIPTION OF THE SEVERAL VIEWS OF THE DRAWINGS

FIG. 1 is a perspective view of a sterilization process challenge device comprising a container, a cap, an insert member, and a biological indicator according to an embodiment;

FIG. 2 is an exploded view of the challenge device of FIG. 1;

Figure 3:
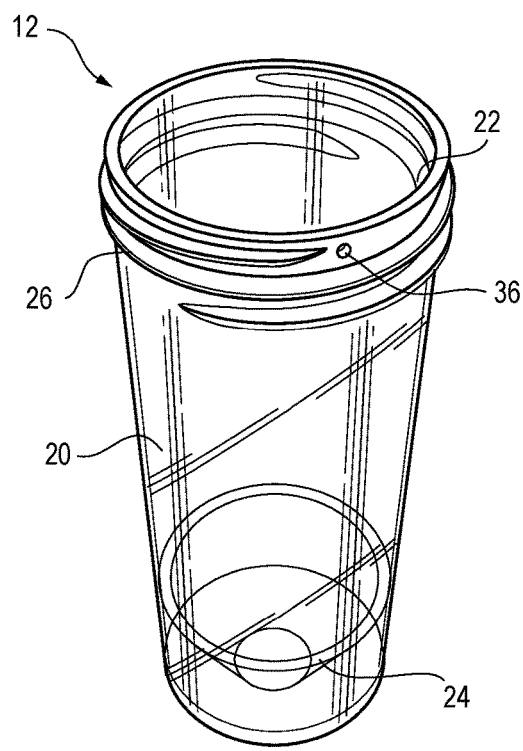
FIG. 3 is a perspective view of the container of FIG. 1.

For simplicity and clarity of illustration, elements shown in the figures may not be drawn to scale. For example, the dimensions of some of the elements may be exaggerated relative to each other for clarity.

DETAILED DESCRIPTION

While the present disclosure is susceptible of embodiment in various forms, there will hereinafter be described presently preferred embodiments with the understanding that the present disclosure is to be considered an exemplification and is not intended to limit the disclosure to the specific embodiments illustrated.

It should be further understood that the title of this section of this specification, namely, "Detailed Description", relates to a requirement of the United States Patent Office, and does not imply, nor should be inferred to limit the subject matter disclosed herein.

A sterilization process challenge device according to various embodiments is provided. The challenge device may be configured to hold a biological indicator and/or a chemical indicator and provide a restrictive fluid flow path to the biological indictor and/or the chemical indicator to test the efficacy of a sterilization process. For example, the challenge device may be configured to hold a biological indicator containing microorganisms, such as *Escherichia coli, Legionella* sp., *Campylobacter* sp., *Staphylococcus, Streptococcus* species and *Cryptosporidium*. The challenge device may be used to verify the efficacy a sterilization process involving steam or a gaseous sterilization sterilant, such as gaseous hydrogen peroxide, gaseous ethylene oxide, and the like.

FIGS. 1 and 2 illustrate a sterilization process challenge device 10 according to an embodiment. FIG. 1 shows the challenge device 10 as assembled and ready for use in a sterilization process cycle, and FIG. 2 is an exploded view of the challenge device 10. The challenge device 10 may generally comprise a container 12, a cap 14, and an insert member 16. The container 12 may define a chamber 20 configured to contain the insert member 16 and at least one sterilization indicator 18.

The at least one sterilization indicator 18 may be a biological indicator and/or a chemical indicator. In the embodiment of FIGS. 1 and 2, the sterilization indicator 18 is a biological indicator. In this embodiment, the container 12 may have a generally cylindrical shaped body. In other embodiments, the container 12 may be configured to have a various shaped body, for example, a generally rectangular shaped body.

As best shown in FIGS. 2 and 3, the container 12 may include a first open end 22, a second closed end 24, at least one external thread 26, and at least one hole 36. The at least one external thread 26 may be provided along an outer surface of the container 12 proximate the first open end 22 and configured to engage at least one internal thread 28 of the cap 14 (FIGS. 2 and 4) to close the first open end 22. In an embodiment, the at least one hole 36 may include a single hole arranged proximate a peripheral edge of the first open end 22 as best shown in FIG. 3. Each of the at least one hole 36 may have a diameter of about 0.01 inches to about 0.02 inches, preferably about 0.012 inches to about 0.018 inches, and more preferably about 0.014 inches to about 0.016 inches. For example, the at least one hole 36 may comprise a single hole having a diameter of about 0.014 inches or a single hole having a diameter of about 0.016 inches.

The container 12 may be formed from a suitable polymeric material, such as polypropylene, polycarbonate, polyester, polyolefin, polystyrene, polyacrylamide, polymethacrylate, poly(methyl)methacrylate, polyimide, polyethylene terephthalate, polybutylene terephthalate, polyvinylchloride, and other similar polymers, or a metallic material such as aluminum. In an embodiment, the container 12 may be formed from polypropylene and may have a wall thickness of about 1/16 inches.

Figure 4:
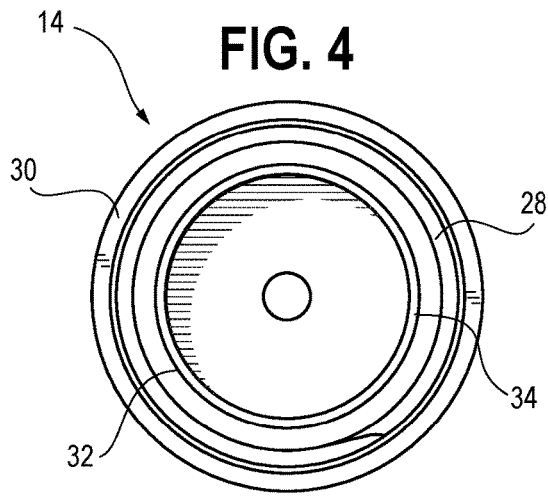
FIG. 4 is a top view of the cap of the challenge device of FIG. 1.
Figure 5:
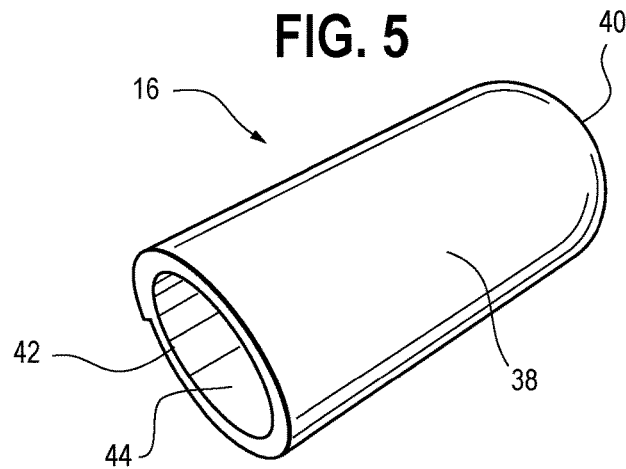
FIG. 5 is a perspective view of the insert member of FIG. 4.

As shown in FIGS. 2 and 4, the cap 14 may include an outer wall 30 and an inner wall 32. The at least one internal thread 28 may be formed along an inner surface of the outer wall 30. The inner wall 32 may be configured to fit in the first open end 22, such that a peripheral portion of the container 12 proximate the first open end 22 may be received in a ring-shaped space 34 defined between the outer wall 30 and inner wall 32. The cap 14 may be formed from a suitable polymeric material, such as polyethylene, polypropylene, polyester, or other similar polymers. In an embodiment, the cap 14 may be formed from polyethylene. The challenge device 10 may be configured such that a fluid path into the chamber 20 may be provided through the at least one hole 36 of the container 12 when the container 12 is closed with the cap 14.

The chamber 20 may be configured to contain the insert member 16 and the sterilization indicator 18, such as a self-contained biological indicator (SCBI). In an embodiment, the insert member 16 may have a body 38 having a generally cylindrical shape, a closed end 40, an open end 42, and a hollow space 44 defined therein. The insert member 16 may be configured to sit generally on top of the sterilization indicator 18 or to receive a portion of sterilization indicator 18. The insert member 16 may be formed from a suitable material, such as rubber, elastomer, or other polymeric materials. In an embodiment, the insert member 16 may be formed from polyvinyl chloride (PVC).

In the embodiment of FIGS. 1-2, the insert member 16 and the biological indicator 18 may be placed in the chamber 20, such that the insert member 16 is arranged adjacent the first open end 22 and the biological indicator 18 is arranged adjacent the closed second end 24. In such an embodiment, the biological indicator 18 may be inserted into the chamber 20 first and the insert member 16 may be subsequently inserted, such that the open end 42 of the insert member 16 may face a cap 19 of the biological indicator 18. In an embodiment, the open end 42 of the insert member 16 may be configured to have a diameter equal to or less than a diameter of the cap 19 of the biological indicator 18, such that the insert member 16 may generally sit on top of the biological indicator 18 when the challenge device 10 is vertically placed with the closed end 24 facing a surface. In the challenge device 10, the insert member 16 may be configured to increase a flow restriction for a gaseous sterilant to reach the biological indicator 18 by providing an additional challenge of removing air captured in the insert member 16, and thereby, delaying a flow of the gaseous sterilant into the chamber 20 to reach the biological indicator 18.

Figure 9:
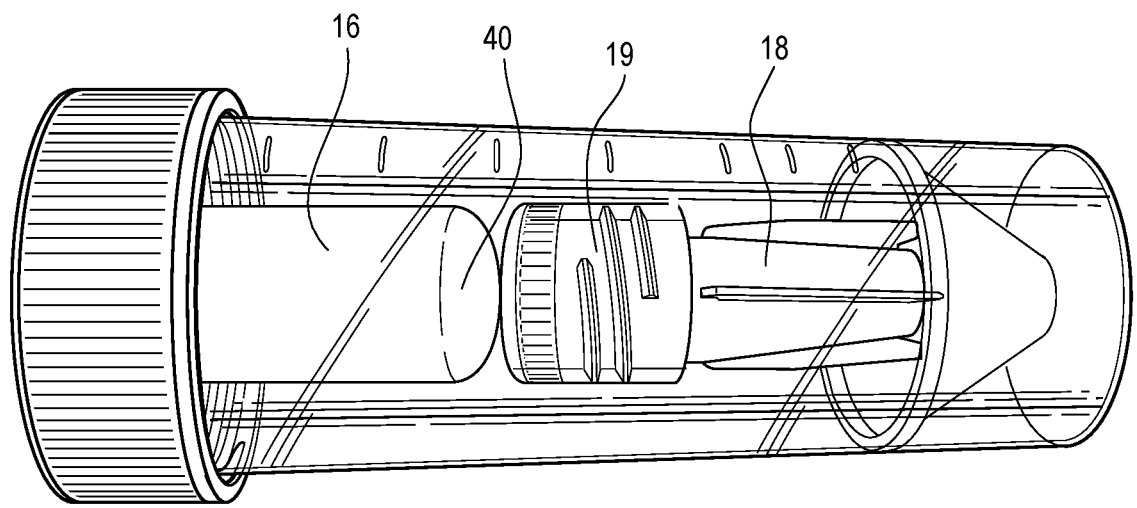
FIGS. 9-15 are perspective views of a sterilization process challenge device according to various embodiments.
Figure 10:
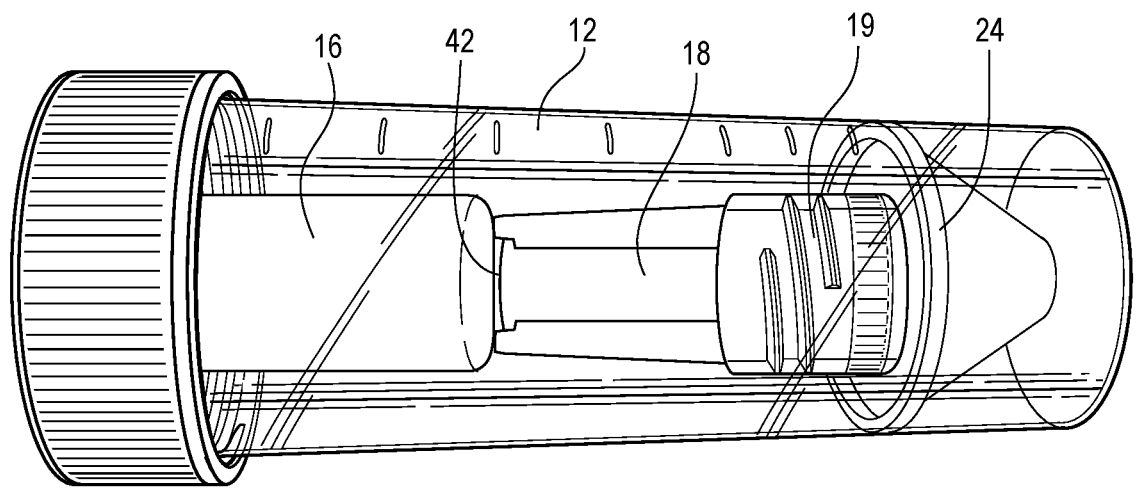
Figure 11:
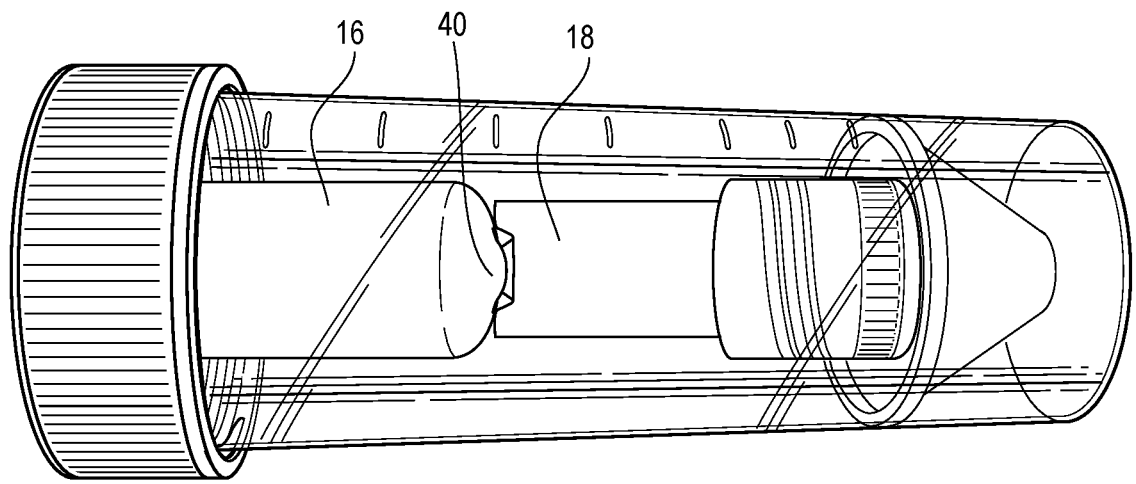
Figure 12:
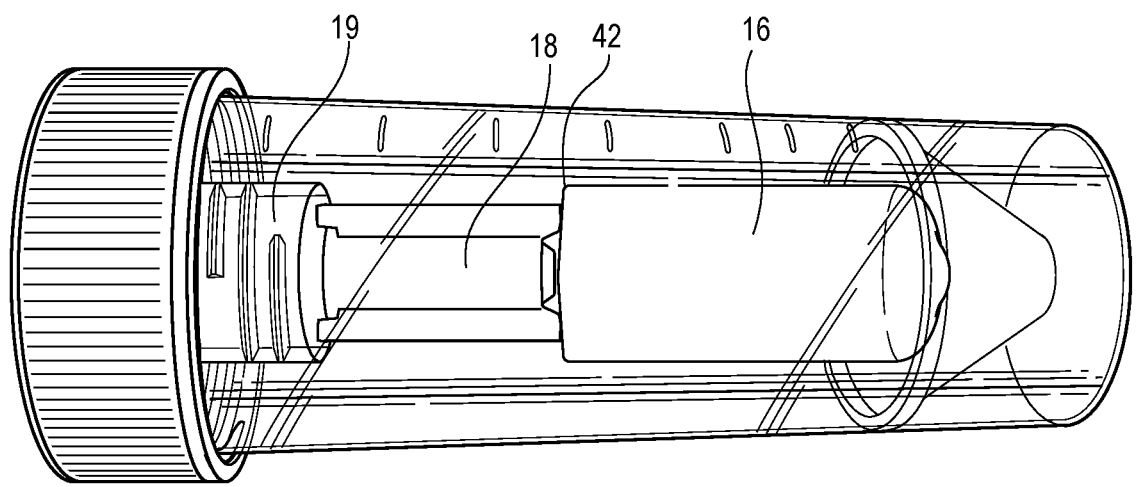
Figure 13:
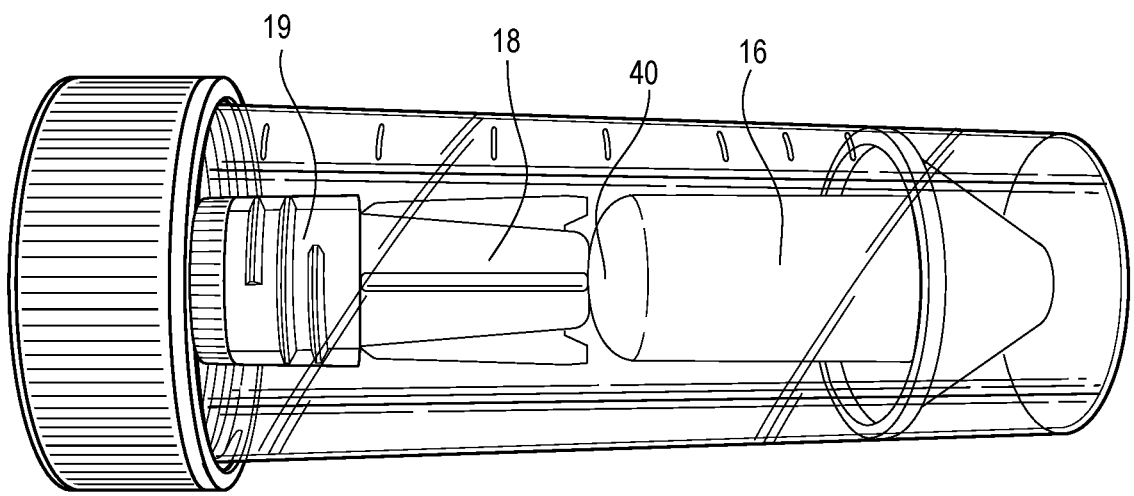
Figure 14:
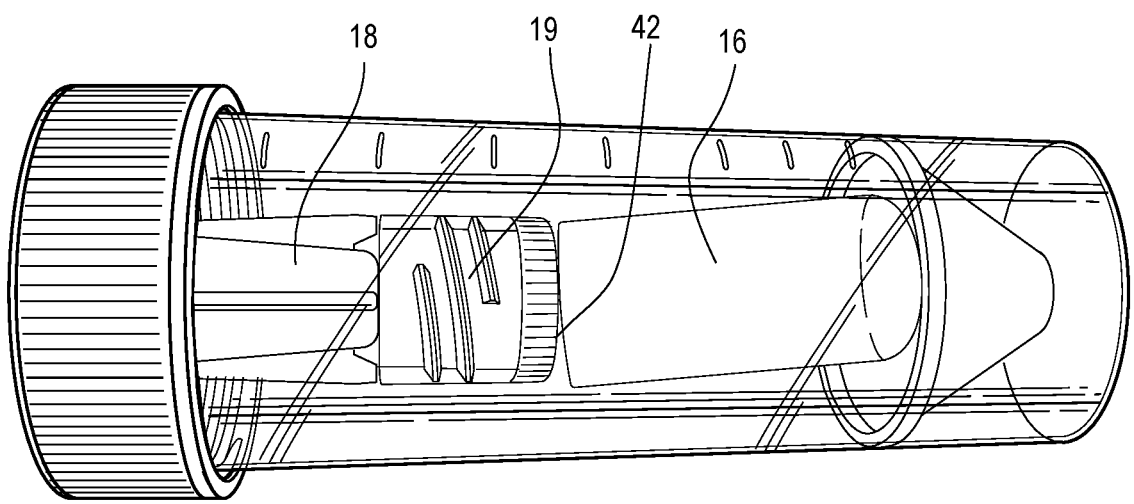
Figure 15:
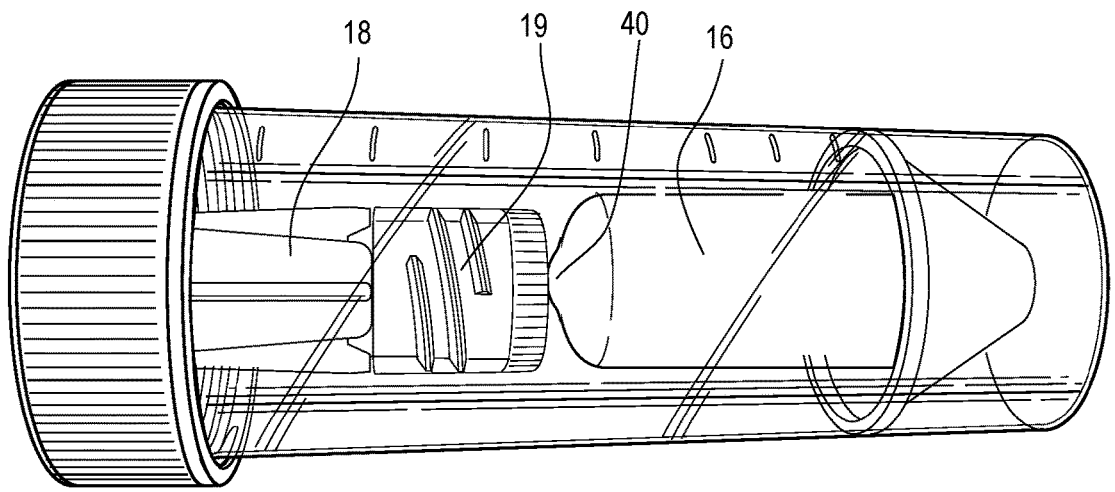

In other embodiments, the insert member 16 and the biological indicator 18 may be placed in the chamber 20 in various arrangements. For examples, the insert member 16 may be arranged adjacent the open end 22 of the container 12 with the closed end 40 of the insert member 16 facing the cap 19 of the biological indicator 18 as shown in FIG. 9. In another embodiment, the biological indicator 18 may be arranged with the cap 19 facing the closed end 24 of the container 12 and the open end 42 of the insert member 16 facing a tail side of the biological indicator 18 as shown in FIG. 10 or the closed end 40 of the insert member 16 facing the tail side of the biological indicator 18 as shown in FIG. 11. In some embodiments, the biological indicator 18 may be arranged adjacent the open end 22 of the container 12. In FIG. 12, the cap 19 of the biological indicator 18 is facing the open end 22 of the container 12 and the insert member 16 is arranged adjacent the biological indicator 18 with the open end 42 facing the tail side of the biological indicator 18. In FIG. 13, the cap 19 of the biological indicator 18 is facing the open end 22 of the container 12 and the insert member 16 is arranged adjacent the biological indicator 18 with the closed end 40 facing the tail side of the biological indicator 18. In FIG. 14, the tail side of the biological indicator 18 is facing the open end 22 of the container 12 and the insert member 16 is arranged adjacent the biological indicator 18 with the open end 42 facing the cap 19 of the biological indicator 18. In FIG. 15, the tail side of the biological indicator 18 is facing the open end 22 of the container 12 and the insert member 16 is arranged adjacent the biological indicator 18 with the closed end 40 facing the cap 19 of the biological indicator 18.

In an embodiment the container 12 may have an inner diameter of about 0.75 inches to about 1.5 inches, preferably about 0.875 inches to about 1.25 inches, and a height of about 2.5 inches to about 4 inches, preferably about 2.75 inches to about 3.25 inches. The insert member 16 may have an inner diameter of about 0.25 inches to about 0.75 inches, preferably about 0.375 inches to about 0.625 inches, and a height of about 0.75 inches to about 1.75 inches, preferably about 1 inch to about 1.5 inches. In the embodiment of FIGS. 1-3, the at least one external threads 26 of the container 12 may be double threads, and the at least one internal threads 28 of the cap 14 may be the matching double threads configured to engage with the external double threads 26.

In an embodiment, the container 12 may be formed from polypropylene and configured to have an inner diameter of about 1.125 inches and a height of about 3.125 inches. The container 12 may also include a single hole 36 having a diameter of about 0.014 inches arranged proximate the first open end 22 and the double external threads 26. The cap 14 may be formed from polyethylene and include the matching double internal threads 28 to engage with the double external threads 26. The insert member 16 may be formed from PVC and configured to have an inner diameter of about 0.5 inches and a height of about 1.25 inches.

Figure 6:
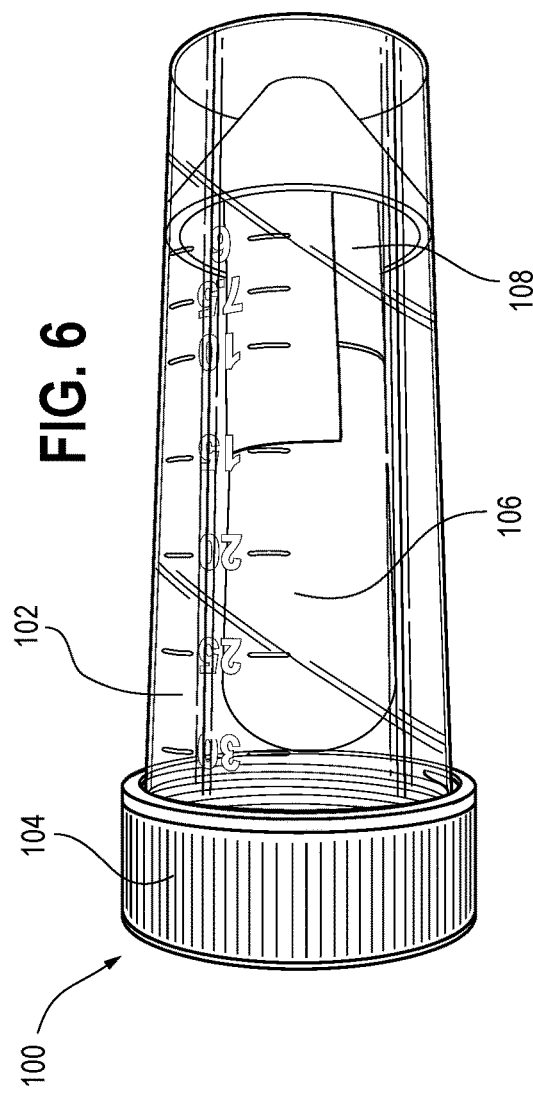
FIG. 6 is a perspective view of a sterilization process challenge device comprising a container, a cap, and an insert member-biological indicator assembly according to another embodiment.
Figure 7:
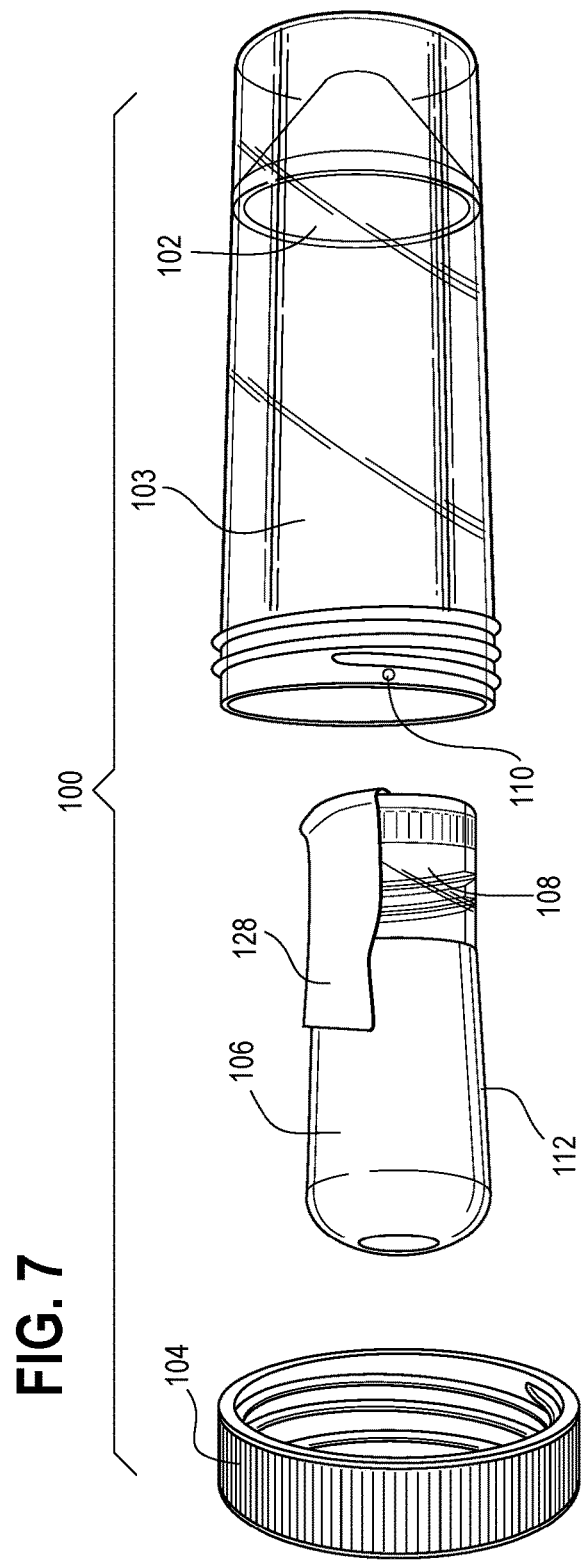
FIG. 7 is an exploded view of the challenge device of FIG. 6.

FIGS. 6 and 7 illustrate a sterilization process challenge device 100 according to another embodiment. The challenge device 100 may be configured similar to the challenge device 10 generally comprising a container 102 having at least one hole 110, a cap 104, and an insert member 106, except in this embodiment the insert member 106 and a biological indicator 108 is provided as a biological indicator assembly 112, wherein at least a portion of a biological indicator 108 is received within and covered by the insert member 106.

Figure 8:
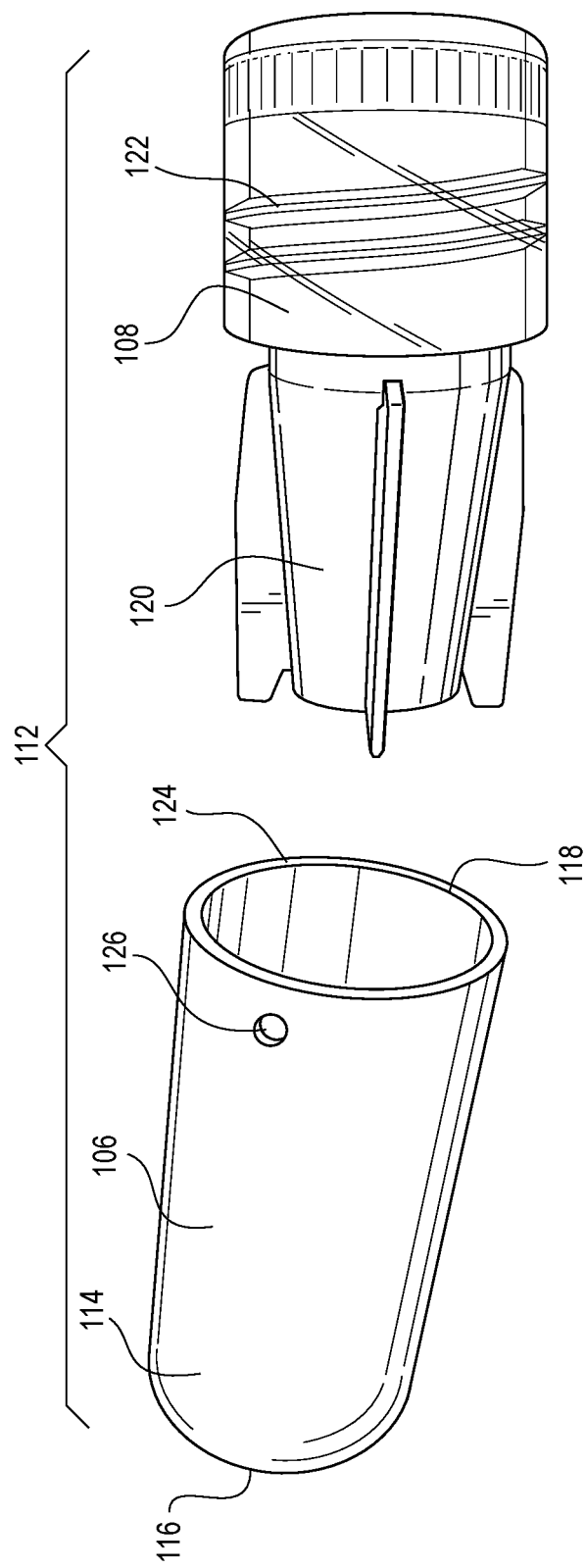
FIG. 8 is an exploded view of the insert member-biological indicator assembly of FIG. 6.

FIG. 8 shows an exploded view of the biological indicator assembly 112. The biological indicator 108 may include a body 120 containing microorganisms and a cap 122. Similar to the insert member 16, the insert member 106 may have a generally cylindrical shaped body 114, a closed end 116, an open end 118, and a hollow space 124 defined therein. In this embodiment, the insert member 106 may further include at least one hole 126. The at least one hole 126 may have a diameter of about 1/32 inches to about 1/8 inches, preferably about 1/16 inches. For example, the at least one hole 126 may include a single hole having a diameter of about 1/16 inches. In the biological indicator assembly 112, the at least one hole 126 may be configured to provide a flow path for air captured in the insert member 108 to exit and a gaseous sterilant to enter the biological indicator assembly 112.

The insert member 106 may be configured to receive a portion of the biological indicator 108. For example, the insert member 106 may be configured to receive the biological indicator 108 through the open end 118 and cover the body 120 of the biological indicator as shown in the FIG. 7. In this embodiment, the biological indicator assembly 112 may be configured such that the open end 118 of the insert member 106 is arranged flush against the cap 122 of the biological indicator 108. In some embodiments, the insert member 106 and the biological indicator 108 may be held together by an indicator tape 128 as shown in FIG. 7.

In FIG. 6, the biological indicator assembly 112 is placed in the container 102 with the biological indicator 108 facing the closed end of the container 102. In other embodiments, the biological indicator assembly 112 may be place in the container 102 with the insert member 106 facing the closed end of the container 102.

In an embodiment, the insert member 16 may be formed from PVC and may be configured to have an inner diameter of about 0.375 inches to about 0.875 inches, preferably about 0.5 inches to about 0.75 inches and a height of about 1 inch to about 2 inches, preferably about 1.25 inches to about 1.75 inches. For example, the insert member 16 may be configured to have an inner diameter of about 0.625 inches and a height of about 1.5 inches.

Figure 16:
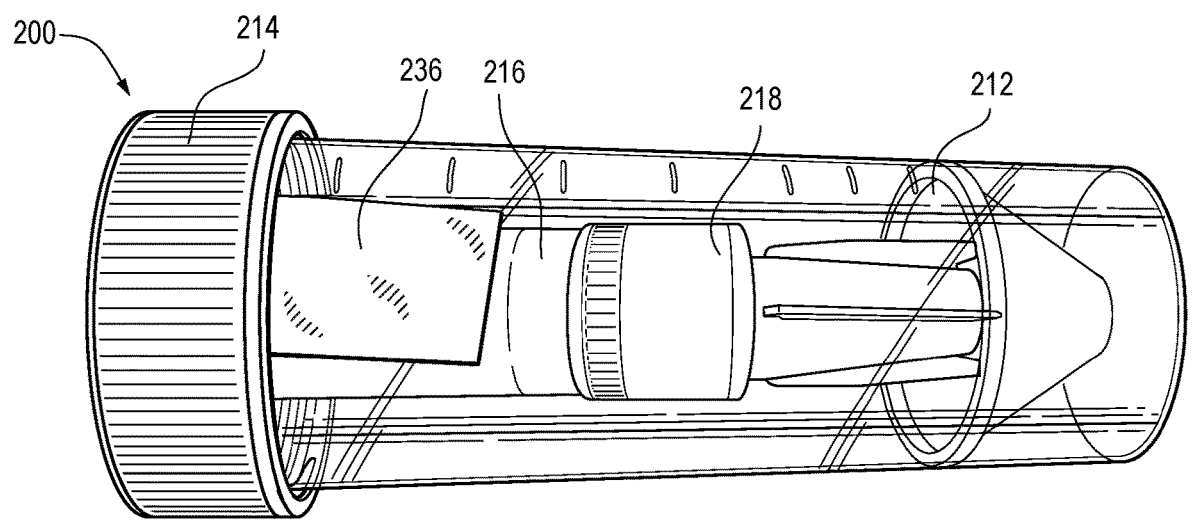
FIG. 16 is a perspective view of a sterilization process challenge device according to yet another embodiment.
Figure 17:
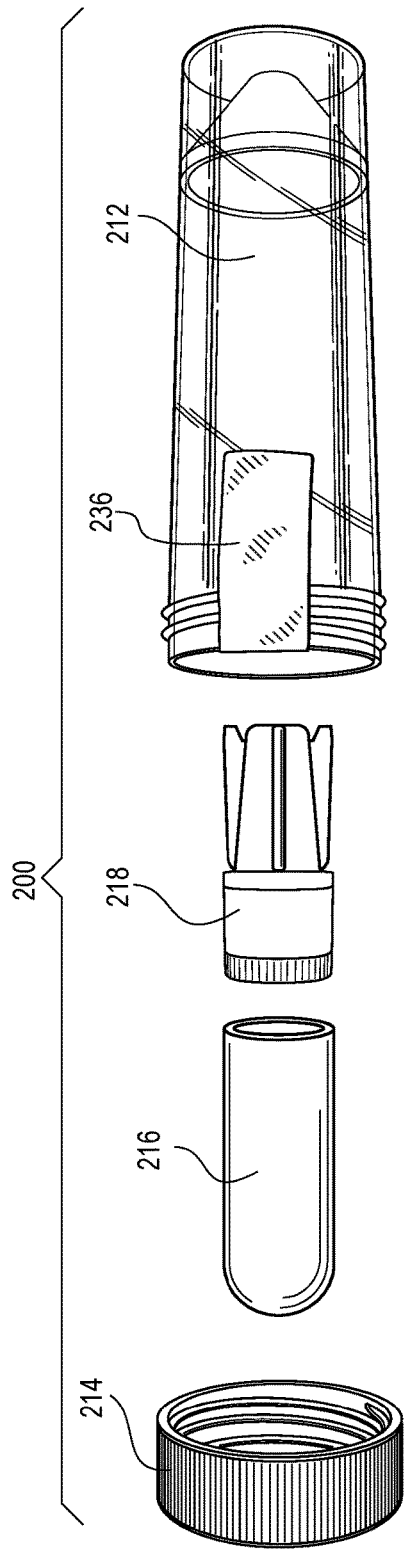
FIG. 17 is an exploded view of the challenge device of FIG. 16.

FIGS. 16 and 17 show a sterilization process challenge device 200 according to yet another embodiment. The challenge device 200 may be configured similar to the challenge device 10 generally comprising a container 212, a cap 214, an insert member 216, and a sterilization indicator 218. In this embodiment, the container 212 may be provided with a spacer member 236 configured to create a gas flow path into the challenge device 10 when the container 212 is closed by engaging the cap 214. The spacer member 236 may be provided instead of the at least one hole 36 of the container 12 or in addition to the at least one hole 36 to form at least one gas flow path. In the embodiment of FIGS. 16 and 17, the gas flow path into the challenge device 200 may be provided only through a gap created by the spacer member 236 without any hole in the container 212.

Figure 18:
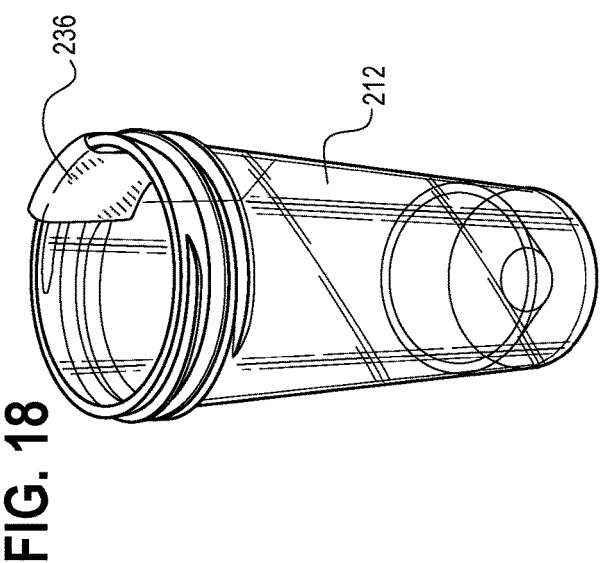
FIG. 18 is a perspective view of the container of FIG. 16.

In an embodiment, the spacer member 236 may be formed from a suitable tape material having a thickness of about 3 mil to about 15 mil, preferably about 5 mil to about 12 mil. FIG. 18 shows the container 212 including the spacer member 236 formed from a piece of a heat resistant tape, which may be attached to the container 212 such that a portion of an open-end periphery of the container 212 is overwrapped and covered by the spacer member 236. In an embodiment, the spacer member 236 may be formed from a tape having a width of about 0.5 inches and a thickness of about 8 mil to about 10 mil. In another embodiment, the spacer member 236 may be formed from a tape having a width of about 0.5 inches and a thickness of about 5 mil. In other embodiments, the spacer member may have a width less than or greater than 0.5 inches.

Figure 19:
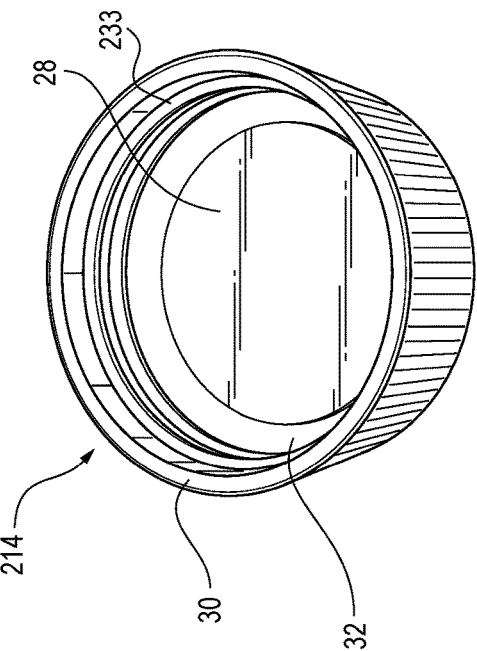
FIG. 19 is a perspective view of a cap according to an embodiment.

The cap 214 may be configured the same as the cap 14 generally including an internal thread 28, an outer wall 30 and an inner wall 32 as shown in FIG. 4. In some embodiments, the cap 214 may also include a sealing member 233 arranged within the inner wall 32 as shown in FIG. 19. The sealing member 233 may be formed from a suitable sealing material, such as an elastomer or rubber, and configured to provide additional fluid sealing property when the container 212 and the cap 214 are engaged with each other.

In the embodiment of FIGS. 16 and 17, the insert member 216 and the biological indicator 218 are placed in the container 212 with the closed end of the insert member 216 facing the open end of the container 212 and the open end of the insert member 216 adjacent the biological indicator 218. In other embodiments, the insert member 216 and the biological indicator 218 may be placed in various arrangements similar to the various arrangements of the insert member 16 and the biological indicator 18 shown in FIGS. 9-15.

In use, the challenge device 10, 100, 200 may be placed in a sterilization chamber along with the objects to be sterilized. A sterilization process may include at least one vacuum phase to remove air from the sterilization chamber followed by introduction of steam or a gaseous sterilant. In an embodiment, a sterilization process includes three vacuum pulses, each pulse followed by introduction of a gaseous sterilant. In such a sterilization process, air in the container 12, 102, 212 may be removed during the vacuum pulses and the gaseous sterilant may flow into the chamber 20, 103 through the at least one hole 36, 110 or a gap created by the spacer member 236. The insert member 16, 106, 216 arranged adjacent the biological indicator 18, 218 or covering a portion of the biological indicator 108 may provide an additional challenge for the gaseous sterilant to reach the sterilization indicator 18, 108, 218.

Challenge device samples were prepared according to the forgoing embodiment of the sterilization process challenge device 100 as shown in FIGS. 6 and 7 and tested in a sterilization process cycle using a hydrogen peroxide gas. Each of the samples comprised a cylindrical container 102, a cap 104, and a biological indicator assembly 112. The cylindrical container 102 was formed from polypropylene and had an inner diameter of about 1.125 inches and a height of about 3.125 inches. Further, the cylindrical container 102 included double external threads and a single hole 110 having a diameter of about 0.014 inches arranged proximate a first open end. The cap 104 was formed from polyethylene and included double internal threads configured to engage with the double external threads of the container 102. The insert member 106 formed from PVC had an inner diameter of about 0.5 inches and a height of about 1.25 inches and includes a single hole 126 having a diameter of about $\frac{1}{16}$ inches. The biological indicator assembly 112 was formed by inserting a body 120 of a biological indicator 108 in the insert member 106 and holding them together with an indicator tape 128. The biological indicator assembly 112 was placed in the container 102, such that the insert member 106 is adjacent an open end of the container 102 and the biological indicator 108 is adjacent a closed end of the container 102, and the container 102 was closed by engaging the cap 104.

The sterilization process cycle was stopped after a ½ cycle for four of the samples and the biological indicators 108 were examined. Each of the biological indicators 108 of the four challenge device samples exhibited a positive growth indicating that the challenge device samples restricted a flow of hydrogen peroxide into the container 102 and prevented it from killing microorganism spores in the biological indicators 108. The sterilization process cycle was stopped after a ¾ cycle for four of the samples and the biological indicators 108 were examined. Each of the biological indicators 108 of these four challenge device samples exhibited a positive growth indicating that the challenge device samples restricted a flow of hydrogen peroxide into the container 102 and prevented it from killing microorganism spores in the biological indicators 108. Finally, the biological indicators for four of the samples were examined after the sterilization cycle was completed. Each of the biological indicators 108 of these four challenge device samples exhibited a negative growth indicating that hydrogen peroxide killed microorganism spores in the biological indicators 108.

Similarly, challenge device samples were prepared according to the forgoing embodiment of the sterilization process challenge device 200 as shown in FIGS. 16 and 17 and tested in a sterilization process cycle using a hydrogen peroxide gas. A first set of the samples including the insert member 216, the biological indicator 218, and the spacer member 236 formed from a tape having a width of about 0.5 inches and a thickness of about 8 mil to about 10 mil were tested in the sterilization process cycles. The biological indicators 218 of these samples exhibited a positive growth after a ½ cycle and a negative growth after a full cycle. Further, a second set of the samples including the biological indicator 218 without the insert member 216 and the spacer member 236 formed from a tape having a width of about 0.5 inches and a thickness of about 5 mil were tested in the sterilization process cycles. The biological indicators 218 of the second set of the samples exhibited a positive growth after a ½ cycle and a negative growth after a full cycle.

All patents referred to herein, are hereby incorporated herein in their entirety, by reference, whether or not specifically indicated as such within the text of this disclosure.

In the present disclosure, the words "a" or "an" are to be taken to include both the singular and the plural. Conversely, any reference to plural items shall, where appropriate, include the singular.

From the foregoing it will be observed that numerous modifications and variations can be effectuated without departing from the true spirit and scope of the novel concepts of the present disclosure. It is to be understood that no limitation with respect to the specific embodiments illustrated is intended or should be inferred. The disclosure is intended to cover by the appended claims all such modifications as fall within the scope of the claims.

What is claimed is:

1. A sterilization challenge device for verifying an efficacy of a sterilization process, comprising:
   a container including a wall, an open end, a closed end, a chamber defined therein;
   a spacer member attached to the container to cover a portion of an open-end periphery of the container;
   a sterilization indicator; and
   a cap configured to engage with the container to close the open end;

wherein the chamber is configured to contain the sterilization indicator, and the spacer member is configured to create a flow path for a gaseous sterilant into the chamber when the open end of the container is closed with the cap, and wherein the spacer member is a tape having a thickness of about 3 mils to about 15 mils.

2. The sterilization challenge device of claim 1, wherein the spacer member is formed from a tape having a thickness of about 8 mil to about 10 mil.

3. The sterilization challenge device of claim 1, wherein the spacer member is formed from a tape having a thickness of about 5 mil.

4. The sterilization challenge device of claim 1, wherein the container is formed from polypropylene and has a generally cylindrical shaped body.

5. The sterilization challenge device of claim 1, wherein the gaseous sterilant is hydrogen peroxide or ethylene oxide.

6. The sterilization challenge device of claim 1, wherein the container includes at least one external thread arranged proximate the open end of the container, and the cap includes at least one internal thread arranged along an outer wall and configured to engage the at least one external thread.

7. The sterilization challenge device of claim 6, wherein the at least one external thread includes double external threads, and the at least one internal thread includes double internal threads configured to engage with the double external threads.

8. The sterilization challenge device of claim 1, further comprising an insert member, and the chamber is configured to contain the insert member and the sterilization indicator.

9. The sterilization challenge device of claim 8, wherein the insert member includes a closed end, an open end, and a hollow space defined therein.

10. The sterilization challenge device of claim 8, wherein the sterilization indicator is a biological indicator, wherein the insert member and the biological indicator are arranged in the chamber such that the insert member sits on top of the biological indicator, wherein the insert member is arranged adjacent the open end of the container and the biological indicator is arranged adjacent the closed end of the container.

11. The sterilization challenge device of claim 8, wherein the sterilization indicator is a biological indicator, wherein the insert member and the biological indicator are arranged in the chamber such that the biological indicator sits on top of the insert member, wherein the biological indicator is arranged adjacent the open end of the container and the insert member is arranged adjacent the closed end of the container.

12. The sterilization challenge device of claim 8, wherein the insert member is formed form polyvinyl chloride and has a generally cylindrical shaped body.

13. The sterilization challenge device of claim 8, wherein the sterilization indicator is a biological indicator, wherein the insert member and the biological indicator are provided as a biological indicator assembly, wherein a portion of the biological indicator is received in the insert member and covered by the insert member.

14. The sterilization challenge device of claim 13, wherein the insert member and the biological indicator are held together with an indicator tape.

15. The sterilization challenge device of claim 13, wherein the biological indicator includes a body containing microorganism and a cap, wherein the body is received in the insert member and covered by the insert member.

16. The sterilization challenge device of claim 15, wherein the insert member includes at least one hole extending through a thickness of the insert member, wherein the at least one hole is configured to provide a flow path for the gaseous sterilant into the biological indicator assembly.

17. The sterilization challenge device of claim 16, wherein the at least one hole of the insert member includes a single hole having a diameter of about 1/16 inches.

* * * * *